(12) United States Patent
Shapiro

(10) Patent No.: US 8,708,993 B1
(45) Date of Patent: Apr. 29, 2014

(54) INFUSION CATHETER PROCEDURE AND SYSTEM

(75) Inventor: Michael Evan Shapiro, Incline Village, NV (US)

(73) Assignee: Physician Technologies, Inc., Reno, NV (US)

( * ) Notice: Subject to any disclaimer, the term of this patent is extended or adjusted under 35 U.S.C. 154(b) by 586 days.

(21) Appl. No.: 10/949,724

(22) Filed: Sep. 24, 2004

Related U.S. Application Data

(63) Continuation-in-part of application No. 10/818,941, filed on Apr. 5, 2004, now abandoned.

(60) Provisional application No. 60/511,730, filed on Oct. 15, 2003.

(51) Int. Cl.
*A61M 31/00* (2006.01)
*A61M 37/00* (2006.01)

(52) U.S. Cl.
USPC .................................. 604/506; 604/131

(58) Field of Classification Search
USPC ............. 604/131, 93.01, 151, 20, 506, 512
See application file for complete search history.

(56) References Cited

U.S. PATENT DOCUMENTS

| | | | | |
|---|---|---|---|---|
| 4,997,420 A * | 3/1991 | LeFevre | | 604/121 |
| 5,207,647 A * | 5/1993 | Phelps | | 604/158 |
| 5,616,133 A * | 4/1997 | Cardenas | | 604/187 |
| 5,695,464 A * | 12/1997 | Viallet | | 604/67 |
| 5,728,070 A * | 3/1998 | Walker et al. | | 604/179 |
| 5,735,829 A * | 4/1998 | Cherian | | 604/264 |
| 5,830,186 A * | 11/1998 | Gonzales et al. | | 604/131 |
| 5,931,809 A * | 8/1999 | Gruber et al. | | 604/512 |
| 5,980,927 A * | 11/1999 | Nelson et al. | | 424/425 |
| 6,099,514 A * | 8/2000 | Sharkey et al. | | 604/264 |
| 6,193,704 B1 * | 2/2001 | Winters | | 604/500 |
| 6,214,370 B1 * | 4/2001 | Nelson et al. | | 424/425 |
| 6,272,370 B1 * | 8/2001 | Gillies et al. | | 600/411 |
| 6,428,529 B1 * | 8/2002 | Gruber et al. | | 604/512 |
| 6,451,335 B1 * | 9/2002 | Goldenheim et al. | | 424/426 |
| 6,565,534 B1 * | 5/2003 | Winters | | 604/151 |
| 6,596,269 B1 * | 7/2003 | Iadarola et al. | | 424/93.2 |
| 6,723,095 B2 * | 4/2004 | Hammerslag | | 606/60 |
| 2001/0049527 A1 * | 12/2001 | Cragg | | 606/61 |
| 2002/0016583 A1 * | 2/2002 | Cragg | | 604/500 |
| 2002/0183722 A1 * | 12/2002 | Harper et al. | | 604/892.1 |
| 2003/0125737 A1 * | 7/2003 | Hammerslag | | 606/60 |
| 2003/0135202 A1 * | 7/2003 | Harper et al. | | 604/892.1 |
| 2003/0181426 A1 * | 9/2003 | Eisenach | | 514/161 |
| 2003/0195518 A1 * | 10/2003 | Cragg | | 606/80 |

(Continued)

OTHER PUBLICATIONS

I. Levack et al., "Abdominal Wound Perfusion for the Relief of Postoperative Pain", *Br. J. Anaesth*, vol. 58, pp. 615-619, 1986.

(Continued)

*Primary Examiner* — Emily Schmidt
*Assistant Examiner* — Michael J Anderson
(74) *Attorney, Agent, or Firm* — The Webb Law Firm

(57) ABSTRACT

The disclosure is directed toward an infusion catheter epidural system comprising a portable infusion pump configured to administer a combination of anesthetics and corticosteroid at a predetermined rate over a predetermined time. A catheter is fluidly coupled to the portable infusion pump. The catheter is configured to be maneuvered into a site of inflammation of a patient to deliver the combination of anesthetics and corticosteroid. The portable pump and the catheter are configured for attachment to the patient.

9 Claims, 3 Drawing Sheets

(56) References Cited

U.S. PATENT DOCUMENTS

| | | | |
|---|---|---|---|
| 2003/0208166 A1* | 11/2003 | Schwartz | 604/266 |
| 2003/0229088 A1* | 12/2003 | Gil et al. | 514/230.5 |
| 2004/0006070 A1* | 1/2004 | Hassenbusch et al. | 514/220 |
| 2004/0220545 A1* | 11/2004 | Heruth et al. | 604/508 |
| 2004/0220546 A1* | 11/2004 | Heruth et al. | 604/508 |
| 2005/0152946 A1* | 7/2005 | Hunter et al. | 424/423 |
| 2005/0169960 A1* | 8/2005 | Hunter et al. | 424/423 |
| 2007/0135768 A1* | 6/2007 | Carlsen | 604/158 |

OTHER PUBLICATIONS

R. C. Franson et al., "Human Disc Phospholipase $A_2$ is Inflammatory", *Spine*, vol. 17, No. 6, Suppl., S:129-132, 1992.

R. Derby et al., "Precision Percutaneous Blocking Procedures for Localizing Spinal Pain. Part II: The Lumbar Neuroaxial Compartment.", *Pain Digest*, vol. 3, pp. 175-188, 1993.

R. Wilkes et al., "Bupivicaine Infusion for Iliac Crest Donor Sites", *Journal of Bone and Joint Surgery*, vol. 3, p. 503, 1994.

J. Woodard et al., "Epidural Procedures in Spine Pain and Management", *Physiatric Procedures in Clinical Practice*, Editors: Hanky and Belfus, pp. 260-291, 1995.

J. Aldrete, MD et al., "Extended Epidural Catheter Infusions with Analgesics for Patients With NonCancer Pain At Their Homes", *Reg. Anesth.*, vol. 22, pp. 35-42, 1997.

Author: Anonymous, "Pain Free Take Aim At the site of Pain . . . Pain Control Infusion Pump", *Sagarlato Labs*, 5 pages, Jul. 1999.

S. Abram et al., "Treatment of Lumbosacral Radiculopathy with epidural Steroids", *Anesthesiology*, vol. 91, No. 6, pp. 1937-1941, Dec. 1999.

Y. Chen et al., "Epidural Steroid Injections: Past, Present, and Future", *Spineline*, Jul.-Aug. 2003, pp. 9-19.

"Guidelines for the Performance of Spinal Injection Procedures", [Internet: http://www.spinalinjection.com/ISIS/standards.htm], 41 pages, printed Dec. 16, 2004.

Ari Ben-Yishay, M.D. Low Back Pain and Sciatica: Radicular Pain, www.spine-health.com Dec. 13, 2005.

McLain, R et al. Epidural Steroid for Back and Leg :Mechanisms of Action and Efficacy. The Spine Journal, 2005;5:191-201.

Kaplan M and Derby R. Epidural Corticosteroid Injections: When, Why, and How. The Journal of Musculosketal Medicine. 1998;39-46.

Papagelopoulos P et al., Treatment of Lumbosacral Radicular Pain with Epidural Steroid Injections. www.orthobluejournal.com Feb. 2001; 24:145-149.

Landau W et al. Assessment: Use of Epidural Steroid Injections to Treat Radicular Lumbosacral Pain: Report of the Therapeutics and Technology Assessment Subcommittee of the American Academy of Neurology—Letter to the Edity. Neurology 2007;69:614-615.

Pauza K et al. Treating Radiculopathy with an Indwelling Epidural Catheter and Infusion Pump. *Pain Physician*.2005;8:271-276.

Boswell M at al. Interventional Techniques in the Management of Chronic Spinal Pain: Evidence-Based Practice Guidelines. *Pain Physician*. 2005;8:1-47.

Abdi S et al. Epidural Steroids in the Management of Chronic Spinal Pain: a Systematic Review. *Pain Physician*. 2007;10:185-212.

Dashfield A et al. Comparison of Caudal Steroid Epidural with Targeted Steroid Placement During Spinal Endoscopy for Chronic Sciatica: A Prospective, Randomized, Double-Blind Trial. *British Journal of Surgery* 2005;4:514-519.

Price C et al. Cost-Effectiveness and Safety of Epidural Steroids in the Management of Sciatica—Executive Summary. *Health Technology Assessment* 2005;9.

Armon C at al. Assessment: Use of Epidural Steroid Injections to Treat Radicular Lumbosacral Pain—Report of the Therapeutics and Technology Assessment Subcommittee of the American Academy of Nerurology. *Neurology* 2007;68:723-729.

Ng et al. The Efficacy of Corticosteroids in Periradicular Infiltration for Chronic Radicular Pain. *Spine* 2005;30:857-862.

Pasqualucci A et al. Epidural Local Anesthetic Plus Corticosteroid for the Treatment of Cervical Brachial Radicular Pain: Single Injection Versus Continuous Infusion. *Clinical Journal Pain* 2007;23:551-557.

Siji T and Beevi S. Epidural Dexamethasone Reduces Postoperative Pain and Analgesic Requirements. *Canadian Journal of Anesthesia* 2006;53:899-905.

Benzon H et al. Comparison of the Particle Sizes of Different Steroids and the Effect of Dilution. *Anesthesiology* 2007;106:331-338.

Nelson D and Landau W. Intraspinal Steroids: History, Efficacy, Accidentality, and Controversy with Review of United States Food and Drug Administration reports 2001;70:433-443.

Shishido H et al. Dexamethasone Decreases Blood Flow in Normal Nerves and Dorsal Root Ganglia. *Spine* 2002;27:581-586.

Depo-Medrol® (methlyprednisolone acetate). Pharmacia & Upjohn Company, Product Insert—revised Jul. 2006.

Dexamethasone Sodium Phosphate. Abraxis Pharmaceutical Products, Product insert—revised Sep. 2006.

Nahaczewski A et al. Dexamaethasone Therapy in Patients with Brain Tumors—A Focus on Tapering. *Journal Neuroscience Nursing* 2004;36:340-343.

Plough B. Home Epidural Analgesic Infusion for Non-Cancer Pain. Journal of Neuroscience Nursing 1995;245-251.

Wheatley R et al. Safety and Efficacy of Postoperative Epidural Analgesia. *British Journal of Anesethesia* 2001;87:47-61.

Dawkins M. An Analysis of the Complications of Extradural and Caudal Block. *Anaesthesia* 1969; 24:554-560.

Edell T et al. Catheters for Neural Blockade: Materials and Designs. *Techniques in Regional Anesthesia and Pain Management* 1998:2:103-110.

DuPen S at al. Infection During Chronic Epidural Catheterization: Diagnosis and Treatment. *Anesthesiology* 1990;173:905-909.

Shapiro M. Infusion Catheter Epidural. *Practical Pain Management* Jan./Feb. 2006.

Weinstein J et al. Surgical vs Nonoperative Treatment for Lumbar Disk Herniation—The Spine Patient Outcomes Research Trial (SPORT): A Randomized Trial. *JAMA* 2006;296:2441-2450.

Derby R et al. Size and Aggregation of Corticosteroids Used for Epidural Injections. *Pain Medicine* 2008;9:227-234.

Kim, S.H. et al., The Effect of Continuous Epidural Block in Lumbago and Sciatica, The Journal of the Korean Pain Society, 1995, pp. 279-285, vol. 8, No. 2.

Article—Infusion Catheter Epidural, Practice Pain Management, Jan./Feb. 2006.

Article—Treating Radiculopathy With an Indwelling Epidural Catheter and Infusion Pump, Pain Physician, 2005.

Article—The Effect of Continuous Epidural Block in Lumbago and Sciatica, Department of Anesthesiology and Pain Clinic, The Journal of the Korean Pain Society, vol. 8, No. 2, 1995.

Article—Epidural Local Anesthetic Plus Corticosteroid for the Treatment of Cervical Brachial Radicular Pain:Single Injection Versus Continuous Injection, Clin/Pain, vol. 23, No. 7, Sep. 2007.

Epidural Infusion Pressure in Degenerative Spinal Disease Before and After Epidural Steroid Therapy; International Anesthesia Research Society, 2002.

Extended Epidural Catheter Infusions With Analgesics for Patients With Noncancer Pain at Their Homes, Regional Anesthesia, vol. 22, No. 1 Jan./Feb. 1997.

Elastomeric Pumps for Ambulatory Patient Controlled Regional Analgesia, Can J Anesth 2000, pp. 897-902.

Steven Richeimer, M.D. *Are Epidural Steriods Useful?*, Pain Update from The Richeimer Pain Institute, Apr. 2000; http://www.helpforpain.com/arch2000apr.htm.

* cited by examiner

INFUSION CATHETER PROCEDURE AND SYSTEM

CROSS-REFERENCE TO RELATED APPLICATIONS

This application is a continuation-in-part of U.S. patent application Ser. No. 10/818,941, filed Apr. 5, 2004 now abandoned, the entirety of which is hereby incorporated by reference, which claims the benefit of U.S. Provisional Application Ser. No. 60/511,730, filed Oct. 15, 2003.

BACKGROUND

Spinal problems are the number one cause of musculoskeletal pain in human beings. Of those, lumbar radiculopathy, sciatica, spinal stenosis, and disc-related pain can be the most disabling and difficult to treat. A variety of treatment options are currently available to patients, including a multitude of medications, physical therapy chiropractics, acupuncture, Pilates, massage, and a variety of other exercise programs and modalities. Despite the variety of treatments, many patients do not respond to these treatments. Consequently, interventional spinal procedures including epidural steroid injections are often the last step before surgery. Fortunately, these injections are successful in up to 80% to 90% of patients who have them performed, and can prevent the patient from undergoing surgery. Unfortunately, 10% to 20% of patients who do undergo lumbar epidurals do not get adequate relief, and often times, surgery is the only last viable option.

What is needed in the art is an alternative to the above-stated treatment options.

SUMMARY

The disclosure is directed toward an infusion catheter system comprising a portable infusion pump configured to administer a combination of anesthetics and an anti-inflammatory agent at a predetermined rate over a predetermined time. The anti-inflammatory agent may be a corticosteroid or may be another type of anti-inflammatory agent. A catheter is fluidly coupled to the portable infusion pump. The catheter is configured to be maneuvered into a site of inflammation of a patient to deliver the combination of anesthetics and corticosteroid. The inflammation site may be the spinal epidural space, sacro-iliac joints, or other inflamed tissues in the spine. The portable pump and the catheter are configured for attachment to the patient.

DETAILED DESCRIPTION

Figures 1, 2:
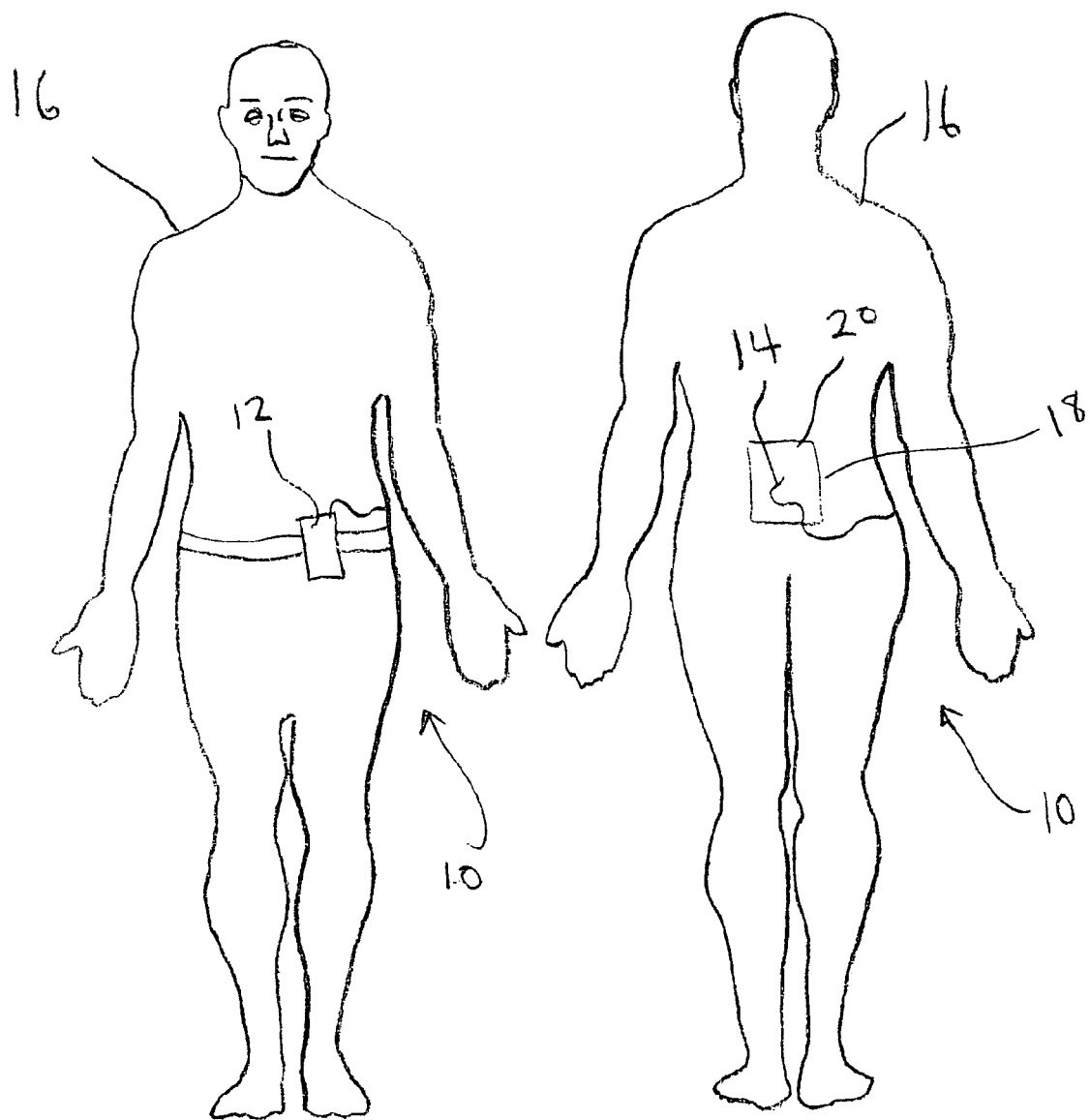
FIG. 1 is an illustration of the front of an exemplary infusion catheter system in use.
FIG. 2 is an illustration of the back of an exemplary infusion catheter system in use.

In determining which patients are candidates for the infusion catheter procedure of the present invention, it is first imperative to understand the pathophysiology behind disc/nerve root pain, indications and benefits, as well as pitfalls of lumbar epidurals.

Lumbar epidural injections have been the treatment of choice for lumbar radiculopathy, as well as discogenic pain for the last 40 to 50 years. By injecting a combination of a corticosteroid, such as Kenalog, Celestone, or Depo-Medrol, and anesthetics, such as lidocaine, into the epidural space as close to the inflamed area as possible, it offers patients a non-operative, safe, and effective way to manage these disabling conditions. It has become a standard of care for the majority of cases of herniated disc/radiculopathy, which are not responsive to conservative measures mentioned above, and is often the last step prior to surgical consideration. Typically, most patients would require anywhere from one to three epidurals for management of the pain over a four to eight week period of time. The epidural spaces are vascular, and thus medications are quickly absorbed intravenously, which often necessitates a second injection, and often times, a third injection. A maximum of four injections may be entertained with a one-year period for maximum pain management.

Radicular pain tends to result from mechanical compression, as well as chemical irritation, to a nerve root. Inflammation may be a key factor precipitating symptoms, even in the presence of mechanical compression, and several different mechanisms of inflammatory response have been postulated. The neurotoxin phospholipase A2 is released from the intact disc after mechanical injury, and can propagate an inflammatory cascade, resulting in both chemotactic and non-cellular responses via leukotrienes and prostaglandins. Pain generation also involves neurogenic inflammation. A variety of neuropeptides, such as substance P and calcitonin gene-related peptide, are activated and released in the dorsal root ganglion following noxious mechanical stimulation, inducing nociceptor sensitization by prostaglandins and leukotrienes. Given this inflammatory basis to both discogenic and particularly radicular pain, epidural injections are utilized for therapeutic purposes, typically including a corticosteroid as mentioned above, which are the most potent anti-inflammatories offered by physicians. Corticosteroids have known anti-inflammatory properties and anti-phospholipase A2 effects involving inhibition and prostaglandin synthesis. Corticosteroids may also impair cell-mediated immunologic responses, block nociceptive C-fiber conduction, reduce ectopic discharges in pathologic nerve roots and block vascular response of vasa nervorum to inflammatory agents. Corticosteroids may also block development of the hyperalgesic state by reducing production of prostaglandins mediating central sensitization, although this effect still remains controversial.

Currently, three portals are available for physicians to deliver the medications into the epidural space. A preferred portal for delivery is the lumbar epidural space. Those portals include the caudal approach, intralaminar, as well as transforaminal. Transforaminal epidurals tend to be an excellent choice when one-level nerve root is involved. Intralaminar approach can also be effective, but often times may be too dorsal. A caudal approach can be effective, particularly from the L4 down to the S1 level, has the advantage of being bilateral, particularly for stenosis an discogenic pain, and also has much less incidence of dural puncture and nerve damage, but often can lead to coccyx pain for a few days following the injection. The pathology involved dictates which approach may be most effective.

To avoid suppression of the hypothalamic-pituitary axis, repeat injections should not be administered more than once every two or three weeks. If there is adequate benefit from the first injection and enough residual pain to warrant further treatment, then a second injection can be repeated in approximately two to three week intervals. If there typically is no response to the first fluoroscopically guided epidural, often times a second injection can be performed. Also, often times, a second but different portal may be chosen if the first injection is not effective. In clinical practice, a third epidural is performed only if the patient should demonstrate a cumulative response to the first epidural, but still has some residual pain and dysfunction. Epidurals can be performed for patients with axial pain without radicular symptoms, again, particularly if the patient should be non-responsive to conservative care and continue to have discogenic type pain, often associated with central disc herniations or annular tears, and degenerative discs.

Despite the success of the epidural, there are several pitfalls. There are a certain percentage of people who receive epidurals (despite the fact that they are performed precisely with fluoroscopic guidance) who do not get any response at all, and continue to be disabled by their pain. There are many patients who may get a very short-lived response, getting relief for a couple of days or a few weeks, and then return quickly to a baseline level, and repeat this pattern despite a second and third epidural. There are also patients who may only get mild to moderate relief following a series of epidurals, and continue to have a moderate or significant degree of disabling pain despite three and even four epidural injections. Consequently, this raises the question as to why epidurals are effective in some of the population, but not effective at all in others.

Obvious reasons may include the chronicity of pain; patients with more acute pain tend to respond more favorably than patients with chronic pain. Patients who are post-surgical tend to not respond as effectively. Patients who tend to have secondary gains, such as Worker's Compensation and personal injury cases, tend not to respond effectively to all treatments, including epidurals. A certain percentage of patients are misdiagnosed, and consequently get an epidural when it may not be indicated. There are also a percentage of people who get the epidural where it may not be performed properly, particularly those who still perform them without fluoroscopic guidance, and therefore, the patient does not receive an effective does of the medication to the point of inflammation. Due to the vascular nature of the epidural space that the medication is quickly absorbed in the majority of the patients, and consequently, many patients do not get enough of the corticosteroid to the inflamed spot for a lengthy period of time to get the adequate amount of anti-inflammatory response necessary.

When a nonionic radiopaque contrast media is injected under fluoroscopic guidance, one can visually see the dye within the epidural space and the nerve root. Often times, when the x-ray is repeated three to five minutes later, the dye is completely gone, which would indicate that is has been completely absorbed. It has been postulated that the same thing happens with medication. That is, even though you may have an adequate amount of corticosteroid in the nerve root or in the epidural space adjacent to the point of inflammation, it gets absorbed so quickly in some patients that they do not get enough of the medication lasting in the inflamed area long enough to give an adequate response. Often times, the response is short-lived, and giving a second and third epidural; does not get the adequate response.

In these cases, the infusion catheter procedure according to the present invention can be very effective. The infusion catheter procedure according to the present invention can significantly reduce the prolongation of symptoms, and disability, as well as significantly reduce the cost by requiring only one procedure instead of two or three. It also can reduce the stress and anxiety of the patient by only having to perform one procedure instead of two or three, and should return to the previous functional status in a more timely fashion.

Figure 4:
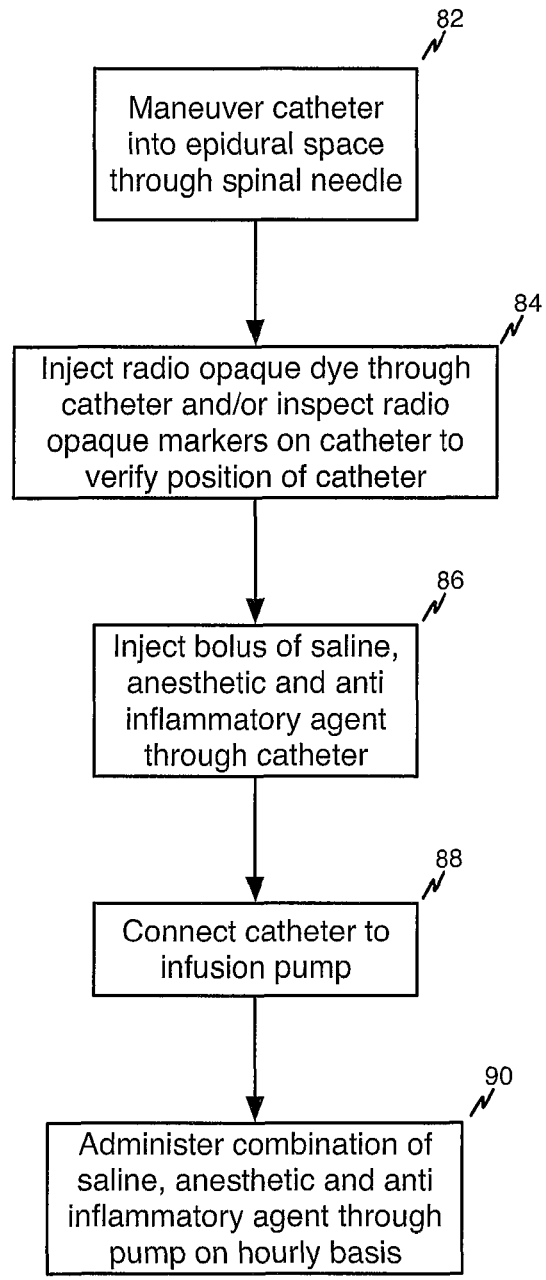
FIG. 4 is a flow diagram showing an illustrative embodiment of an infusion catheter procedure according to the present invention.

The concept behind infusion catheter procedure according to the present invention can easily be seen with reference to FIG. 4, a flow diagram showing an illustrative embodiment of an infusion catheter procedure according to the present invention. At reference numeral 82, a catheter is maneuvered into the epidural space through a spinal needle. A catheter can easily be maneuvered through a 3.5-inch #18 or #20 gauge spinal needle into the epidural space, the sacro-iliac joints, or other inflamed spinal tissue, utilizing either an intralaminar, transforaminal, or caudal approach depending on the site of inflammation to the inflamed area. At reference numeral 84, the position of the catheter is verified. Verification can be easily obtained utilizing a radiopaque contrast media, which when injected through the catheter, can be visualized in the epidural space under fluoroscopy. The catheter will also have radiopaque markers on it for further verification should that be necessary. At that time, as shown at reference numeral 86, a bolus of saline, anesthetic and an anti-inflammatory agent will be injected through the catheter to begin the pain management process. The anti-inflammatory agent may be a corticosteroid or may be another anti-inflammatory agent, for example ketoralac, marketed by Roche Pharmaceuticals under the brand name Toradol. The anesthetic should serve to dramatically reduce the patient's pain and thereby assist with both diagnosis and proper placement of the catheter. Once proper placement of the catheter has been determined, the catheter will be hooked up to a portable infusion pump as indicated at reference numeral 88. The catheter will also be taped adequately to the patient to reduce the risk of any motion of the catheter. As shown at reference numeral 90, the infusion pump will then administer a combination of anesthetics and anti-inflammatory agent on an hourly basis through the catheter and to the affected region over about a 72-hour period. At that time, the patient will return to the clinic and have the catheter removed. By utilizing the procedure of the present invention, this ensures that the inflamed site will be bathed in corticosteroid on a constant basis over a 72-hour period, and should also ensure that the inflamed area will have potential maximal response to the anti-inflammatory effects of the steroid during this time.

As an example of the procedure of the present invention where corticosteroid is employed as an anti-inflammatory agent, a total of about 5 cc. of about 40 mg/cc of Kenalog or about 5 cc. of about 6 mg/cc of Celestone may be employed. Initially, about a 2 cc. bolus of the steroid will be injected during this initial phase, and the remaining about 3 cc. will be administered in divided doses over the next 72-hours. The anesthetic will be lidocaine 1%, preservative-free, which will be administered with the initial about 5 cc. bolus, and then about 1 cc. per hour over the next 72-hours for a total of about 77 cc. of lidocaine over a 72-period of time. Since the elimination of lidocaine following the intravenous bolus is about 1.5 to about 2 hours, and the maximum recommended individual dose should not exceed about 4.5 mg/kg of body weight, this ensures that the amounts are well below the toxic level of lidocaine over the three-day period. In general, it is recommended that a maximum dose of lidocaine not exceed about 300 mg. for a one-time bolus. Over a 72-hour period of time, at that low level of flow rate, this amount should not pose any danger or significant risk to the patient. Since lidocaine is metabolized in the liver, certainly any patients with significant liver pathology could be and would be excluded from use.

In using the procedure of the present invention, the inflamed nerve root and disc can be infused with a steady does of anesthetic and anti-inflammatory agent over the 72-hour period as opposed to a one-time bombardment as it is typically done. This method offers the patient a greater chance of maximal pain relief and resolution of their inflammatory condition. Because the epidural space is vascular, during the traditional epidural, the medication is quickly absorbed systemically and therefore, only a small percentage of the loading dose into the epidural space is actually absorbed by the inflamed tissue. By utilizing procedure of the present invention, this will happen to some degree as well, but repeated injections of anesthetic and corticosteroid in divided doses on an hourly basis for 72-hours, results in a greater amount of the corticosteroid will be presented to the inflamed tissue, and consequently will offer the patient a greater degree of success for reducing pain and reducing the risk of necessitating a second or third procedure. This should also be true when pain management of sacro-iliac joints and other spinal tissues is provided according to the present invention.

The biggest concern of any physician is the welfare of the patients. The procedure of the present invention is no more risky to the patient than a standard lumbar epidural. Epidurals in general are very safe, and the risks include allergic reaction, infection, transient paresis, paralysis, hematoma, transient hyperglycemia, increased pain, arachnoiditis, and nerve damage. In addition, because the patient will have a steady flow of lidocaine for three days, his or her pain will be masked for a prolonged period, which will further assist in the long-term benefit of the procedure of the present invention by blocking the pain channels and by closing the pain gate. Therefore, it would be very important to educate and thoroughly explain to the patient that he or she must avoid any activity or position typically that would aggravate his or her pain.

For example, increased radicular symptoms occur after sitting for more than 20 minutes, and the patient must avoid sitting for greater than 20 minutes while the infusion pump is being utilized. This will greatly reduce the risk of further damage to the nerve root while utilizing the procedure of the present invention. The risk of infection is currently very minimal utilizing infusion pumps for postoperative pain, and occurs rarely. The use of the procedure of the present invention provides for a preoperative setting where there is no surgical destruction of tissue. There is no significant increased risk of infection utilizing procedure of the present invention versus a typical epidural. Putting the patients on antibiotics, such as Keflex 500 mg. t.i.d., for the three-day period while they are undergoing the treatment can even further reduce this risk. Aside from the two examples noted above, there are no additional risks to performing the procedure of the present invention versus a standard lumbar epidural.

Any patient who is currently a candidate for a lumbar epidural would be considered a candidate for the procedure of the present invention. By utilizing the procedure of the present invention versus the current standard epidural, the need for a $2^{nd}$ or $3^{rd}$ procedure is greatly reduced. The procedure of the present invention offers the patient the potential for a more thorough and lasting degree of pain relief than the "standard" epidural currently available to patients. The downside of implementing the procedure of the present invention is negligible for sacro-iliac joints and other spinal tissue sites as well as epidural sites.

Figure 3:
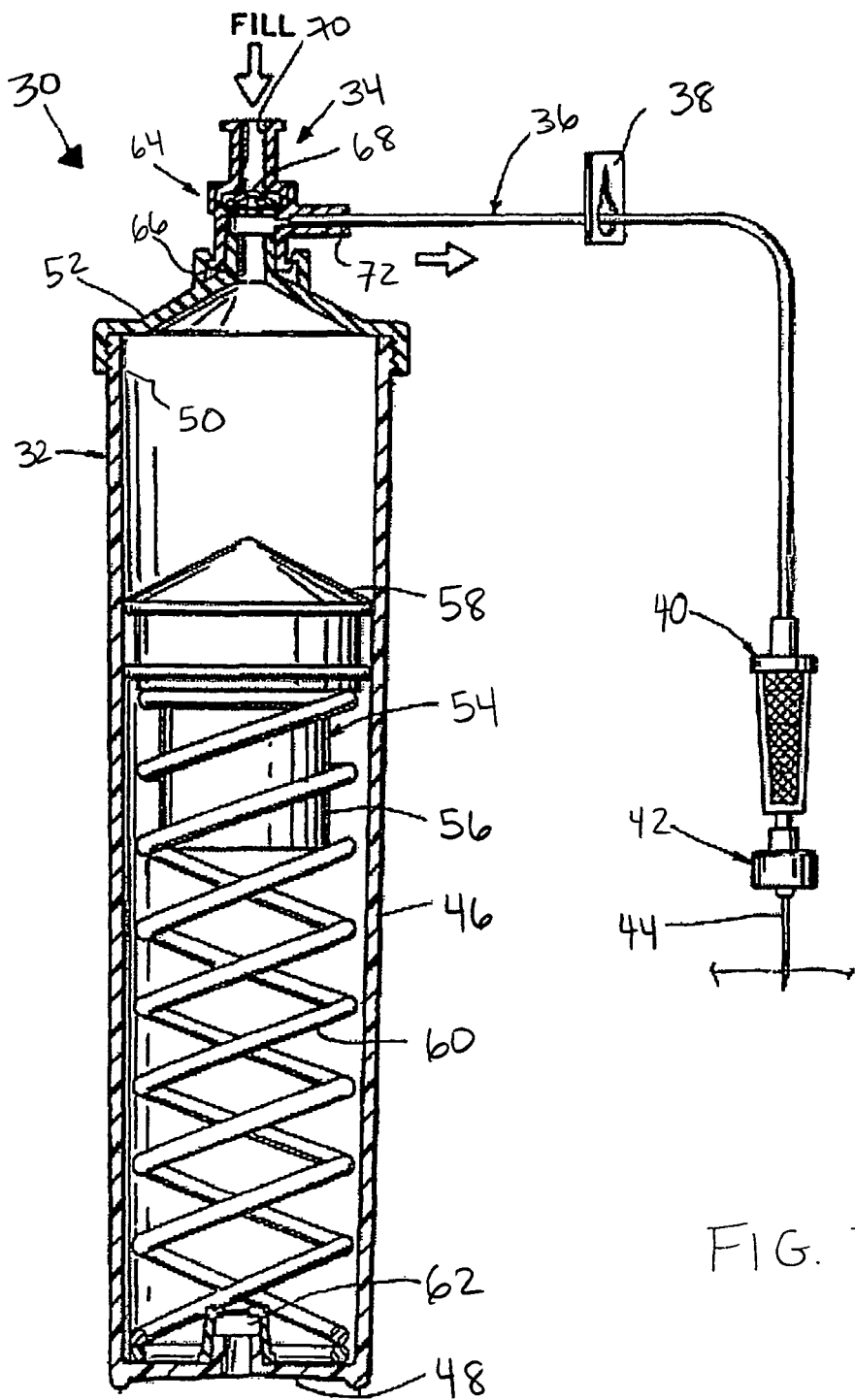
FIG. 3 is a cross-sectional view of an exemplary infusion catheter in accordance with this invention.

Referring to FIGS. 1 and 2, illustrations of an exemplary infusion catheter epidural system are shown. The infusion catheter system 10 includes at least one pumping means 12, and preferably, an infusion pump, such as a 200 ml medication reservoir pump. The pumping means 12 is fluidly coupled to a delivery means 14, preferable a catheter. The catheter 14 can be inserted into a site of inflammation (not shown) of a patient 16. The embodiment illustrated, demonstrates the use of the system 10 proximate the lower back region, however, other regions of the body of the patient having sites of inflammation are also contemplated. The catheter 14 is coupled to the skin 18 of the patient 16 by use of adhesive tape 20 or other fastening means. The pumping means 12 is configured to administer medication through the delivery means 14 at a predetermined rate of delivery and over predetermined duration of time. As disclosed above, the medication can be injected on an hourly basis over a 72 hour duration. The pumping means 12 can be worn about the waist by the patient while the catheter is secured to the lower back. The pumping means 12 includes failsafe features to ensure the proper delivery of the medication. A suitable pump is found in U.S. Pat. No. 4,997,420, incorporated herein by reference. FIG. 3 illustrates an apparatus 30 includes a syringe pump 32 connected through a one-way valve 34 with a length of tubing 36 having a slide clamp 38 thereon. In the form of invention shown in FIG. 3, a cone filter assembly 40 is attached to the distal end of the length of tubing and an adapter and restrictor 42 is attached to the cone filter assembly 40. A length of tubing 44 is attached to the adapter 42.

The syringe pump 32 comprises a two-piece housing having a barrel 46 with a closed end 48 and an open end 50, with a top 52 attached to the open end 50. A piston 54 is reciprocal in the barrel 46 and comprises a plastic plunger 56 having a rubber tip 58 for sliding engagement with the inner surface of the barrel wall. The piston 54 is urged toward the open end 50 of the barrel 46 by a compression spring 60 engaged between the plastic plunger 56 and the closed end 48 of the barrel 46.

The barrel 46 has a reverse taper, being smaller in diameter at its closed end than at its open end, whereby the frictional drag on the piston becomes less as the spring expands and pushes the piston toward the open end of the barrel. This taper on the barrel side wall is calculated to cooperate with the spring characteristics so that the reduction in force imparted by the expanding spring is compensated by the reduction in frictional drag between the piston and barrel side wall, achieving a constant force on the material being dispensed by the pump throughout the length of travel of the piston.

The separate cap or barrel top 52 enables the spring 60 and piston 54 to be assembled in the barrel 46, after which the cap 52 is permanently affixed to the open end 50 of the barrel 46.

An air vent filter 62 is placed in the closed end 48 of the barrel 46 to vent air from the barrel as the piston is being forced to the bottom of the barrel during loading of the syringe, and also relieves vacuum in the barrel as the spring expands and pushes the piston upwardly in the barrel during a dispensing cycle. The barrel is preferably transparent and has scale markings thereon so that the quantity of drug in the syringe, and conversely, the quantity of drug administered may be visually observed.

A one-way T valve 64 is attached to the cap 52 for admitting the drug to the syringe while it is being loaded, and through which the drug is dispensed during a dispensing cycle. This valve is snap-fitted to the cap 52 by snap detents 66, and includes a flexible disc 68 which functions as a one way valve to admit drug to the syringe through an inlet fitting 70 but which prevents reverse flow therethrough. Drug flows outwardly through the valve via an outlet port 72.

In operation, the slide clamp 38 is closed and the liquid containing drug is forced through the one way valve 34 into the syringe, forcing the piston downwardly in the barrel and compressing the spring 60. Air behind the piston escapes through the air vent 62. When the syringe is filled the slide clamp is opened to clear any air in the length of tubing 36. When the air has been cleared, the slide clamp is again closed.

After the needle has been positioned by the physician in the desired location, the catheter is pushed into the end of the needle. The catheter exits the needle tip into the desired location. The needle is then removed and the catheter is taped into place. The catheter is attached to the regulator 42. The pump will then dispense the appropriate amount of medication to the patient until the catheter is removed by the physician.

It is contemplated that patients can include animals as well as humans. The site of inflammation can be in the lower back as well as in spinal joints and in other locations requiring administering the system 10.

While embodiments and applications of this system have been shown and described, it would be apparent to those skilled in the art that many more modifications than mentioned above are possible without departing from the inventive concepts herein. The invention, therefore, is not to be restricted except in the spirit of the appended claims.

What is claimed is:

1. A method of treating inflammation in the epidural space of a patient, the method comprising:
    providing an infusion pump;
    accessing the epidural space of a patient with a needle;
    maneuvering a catheter having radiopaque markers into the epidural space through the needle;
    positioning the catheter within an inflamed region of the epidural space, wherein the positioning comprises viewing the radiopaque markers under fluoroscopy and injecting a radiopaque contrast media through the catheter and into the epidural space under fluoroscopy;
    injecting a bolus dose of an anti-inflammatory agent into the epidural space through the catheter;
    connecting the infusion pump to the catheter after the injection of the bolus dose;
    securing the catheter to the patient to reduce the risk of any motion of the catheter; and
    delivering a quantity of an anti-inflammatory agent from the infusion pump to the inflamed region of the epidural space through the catheter continuously over a period of time, wherein the volume of a fluid containing the anti-inflammatory agent delivered continuously over the period of time is greater than the volume of fluid containing the anti-inflammatory agent delivered in the bolus dose.

2. The method of claim 1, wherein the injecting of the bolus dose further comprising injecting an anesthetic.

3. The method of claim 2, wherein the anesthetic, the anti-inflammatory agent and saline are injected simultaneously as a bolus.

4. The method of claim 1, further comprising repositioning, if necessary, the location of the catheter within the epidural space after the injection of the radiopaque contrast media and prior to the connection of the infusion pump to the catheter.

5. The method of claim 1, further comprising putting the patient on an antibiotic during the period of time.

6. A method of treating inflammation in the epidural space of a patient, the method comprising:
    accessing the epidural space of a patient using a needle;
    maneuvering a catheter having radiopaque markers into the epidural space through the needle;
    positioning the catheter within an inflamed region of the epidural space, wherein the positioning comprises viewing the radiopaque markers under fluoroscopy and injecting a radiopaque contrast media through the catheter and into the epidural space under fluoroscopy;
    providing an infusion pump;
    injecting a bolus dose of an anti-inflammatory agent into the epidural space through the catheter;
    connecting the infusion pump to the catheter after the injection of the bolus dose;
    delivering a quantity of an anti-inflammatory agent from the infusion pump to the inflamed region of the epidural space through the catheter continuously over a period of about 72 hours, wherein the quantity delivered from the infusion pump is of a greater volume than the bolus dose.

7. The method of claim 6, further comprising repositioning, if necessary, the location of the catheter within the epidural space after the injection of the radiopaque contrast media and prior to the connection of the infusion pump to the catheter.

8. The method of claim 6, further comprising injecting a bolus dose of anti-inflammatory agent to the epidural space prior to delivering the anti-inflammatory agent continuously over the period of time, wherein the volume of a fluid containing the anti-inflammatory agent delivered continuously over the period of time is about 1.5 times the volume of fluid containing the anti-inflammatory agent delivered in the bolus dose.

9. The method of claim 6, further comprising putting the patient on an antibiotic during the period of about 72 hours.

* * * * *